United States Patent [19]
Thompson et al.

[11] Patent Number: 5,431,667
[45] Date of Patent: Jul. 11, 1995

[54] GAS-SEALED INSTRUMENTS FOR USE IN LAPAROSCOPIC SURGERY

[75] Inventors: Todd A. Thompson, San Jose; Tim Kovac, Los Gatos, both of Calif.

[73] Assignee: Origin Medsystems, Inc., Menlo Park, Calif.

[21] Appl. No.: 26,445

[22] Filed: Mar. 4, 1993

Related U.S. Application Data

[63] Continuation-in-part of Ser. No. 908,709, Jul. 2, 1992, abandoned, which is a continuation-in-part of Ser. No. 888,723, May 26, 1992, Pat. No. 5,192,288.

[51] Int. Cl.⁶ ............................................. A61B 17/04
[52] U.S. Cl. ..................... 606/142; 606/139; 606/141
[58] Field of Search ............... 128/4, 6; 606/139–144; 227/19

[56] References Cited

U.S. PATENT DOCUMENTS

| | | | |
|---|---|---|---|
| 3,777,538 | 12/1973 | Weatherly et al. | |
| 3,882,854 | 5/1975 | Hulka et al. | 128/6 |
| 4,027,510 | 6/1977 | Hiltebrandt | 128/6 |
| 4,550,715 | 11/1985 | Santangelo et al. | 128/4 |
| 4,944,443 | 7/1990 | Oddsen et al. | 227/19 |
| 5,100,420 | 3/1992 | Green et al. | 606/142 |
| 5,171,247 | 12/1992 | Hughett et al. | 606/142 |

Primary Examiner—Gary Jackson
Attorney, Agent, or Firm—Limbach & Limbach; Ian Hardcastle

[57] ABSTRACT

An gas-sealed instrument for use in laparoscopic procedures in a gas-insufflated body cavity. The instrument comprises a static portion, a moving portion, and a flexible seal for preventing gas from escaping from the body cavity through the static portion. The static portion includes a handle, and an elongate outer tube having a bore, a proximal portion attached to the handle, and a distal portion adapted for inserting into the body cavity. The moving portion includes an operating lever pivotally mounted in the handle, and an elongate operating rod mounted in the bore of the elongate outer tube, and sliding axially relative thereto in response to the operating lever. The flexible seal includes an outer portion attached to the static portion, an inner portion disposed about part of the moving portion, and a flexible mid portion between the outer portion and the inner portion. A rigid seal may be substituted for the flexible seal.

38 Claims, 10 Drawing Sheets

GAS-SEALED INSTRUMENTS FOR USE IN LAPAROSCOPIC SURGERY

This application is a Continuation-in-Part of U.S. patent application Ser. No. 07/908,709, filed 2 July 1992, now abandoned, which is a Continuation-in-Part of U.S. patent application Ser. No. 07/888,723, filed 26 May 1992.

BACKGROUND OF THE INVENTION

In laparoscopic procedures performed in the abdomen, working space is provided by insufflating the abdomen using a pressurized gas, such as carbon dioxide. The gas pressure, typically about 15 mm Hg, raises the abdominal wall by several inches, which provides a space into which instruments can be inserted through trocar tubes for visualization and to perform surgical procedures. To prevent the insufflation gas from escaping, each trocar tube forms a gas-tight seal with the abdominal wall, and with the instrument passed through it.

Instruments for use in laparoscopic surgery in which insufflation is used must also be gas tight to prevent the insufflation gas from escaping. A number of laparoscopic instruments, such as clip appliers and forceps, have two components passing through the trocar tube, an outer tube on which a static part of the instrument is mounted, and an operating rod that operates the moving part of the instrument. The operating rod is mounted inside the outer tube and must be capable of freely moving axially relative to the outer robe. Alternatively, the operating rod may operate two opposed moving parts, and the static part may support the moving parts.

The outer robe is shaped to form a gas-tight seal with a trocar tube, but, absent a suitable seal, the space between the operating rod and the outer tube provides a path for insufflation gas to escape through the instrument.

Two-component laparoscopic instruments also include a handle to which the outer robe is attached, and an operating lever, pivoting in the handle, to which the operating rod is connected. Moving the operating lever relative to the handle moves the operating rod axially, and operates the moving part of the instrument.

It is known to provide a grease seal between the outer tube and the operating rod. U.S. Pat. No. 5,100,420 shows the operating rod of a clip applier passing through a closely fitting rectangular aperture in a sealing block installed in the outer tube. The space between the operating rod and the sealing block is fried with silicone grease to prevent insufflation gas leaking between the operating rod and the sealing block.

A grease seal mounted in the outer robe has several disadvantages. A grease seal is short lived; the seal may start to leak after as few as twenty operating cycles. An instrument having a grease seal cannot be re-used, because the grease seal cannot be autoclaved U.S. Pat. No. 4,027,510 shows a clip applier with a pair of sealing tings. Each sealing ring is placed in an annular groove in a widened portion at opposite ends of the operating rod. The sealing rings slide with the operating rod relative to the outer tube to provide a gas-fight seal between the operating rod and the outer tube.

OBJECTS AND SUMMARY OF THE INVENTION

It is an object of the invention to provide an improved gas-tight seal for two-component laparoscopic instruments such as clip appliers and forceps.

It is a further object of the present invention to provide a gas-tight seal for two-component laparoscopic instruments that has greater durability than a grease seal.

It is a further object of the present invention to provide a gas-tight seal for two-component laparoscopic instruments that is located in the proximal part of the outer tube or in the handle of the instrument.

Accordingly, the invention provides an instrument for use in laparoscopic procedures in a gas-insufflated body cavity. The instrument comprises a static portion, a moving portion, and a flexible seal for preventing gas from escaping from the body cavity through the static portion. The static portion includes a handle, and an elongate outer tube having a bore, a proximal portion attached to the handle, and a distal portion adapted for inserting into the body cavity. The moving portion includes an operating lever pivotally mounted in the handle, and an elongate operating rod mounted in the bore of the elongate outer tube, and sliding axially relative thereto in response to at least one of the handle and the elongate outer tube of the operating lever. The flexible seal includes an outer portion attached to the static portion, an inner portion disposed about part of at lest one of the operating lever and the elongate operating rod of the moving portion, and a flexible mid portion between the outer portion and the inner portion.

In a variation, the flexible seal extends into the handle from the proximal portion of the outer tube, the outer portion of the flexible seal is attached concentrically to the proximal portion of the outer tube, and the inner portion of the flexible seal is disposed about the operating rod.

In a further variation, a duckbill seal accommodated in the bore of the proximal portion of the outer tube provides the flexible seal. A flanged portion of the duckbill seal is attached to the bore of the proximal portion of the outer tube, and a nose portion of the duckbill seal is disposed about the operating rod. The operating rod slides within the nose portion of the duckbill seal.

In a further variation, a wiping seal disposed in the bore of the proximal portion of the outer robe provides the flexible seal. The wiping seal has a curved outer portion attached to the bore of the proximal portion of the outer robe, and an ribbed inner portion disposed about the operating rod. The operating rod slides within the ribbed inner portion of the wiping seal.

In a further variation, the operating lever includes a piston coupled to the operating rod. The inner portion of the flexible seal is disposed about the piston, and the outer portion of the flexible seal is attached to the handle. The inner portion of the flexible seal may fit over the piston or may engage in a groove in the piston. The outer portion of the flexible seal may fit into a groove inside the handle molding, or may fit into an insert inside the handle. Alternatively, the outer portion of the flexible seal may be attached inside the handle either directly or may include a stiff annulus attached to the inside of the handle.

In a further variation, the operating lever includes an internal portion housed within the handle. The outer portion of the flexible seal is attached within the handle adjacent to the internal portion of the operating lever, and the inner portion of the flexible seal is disposed about the internal portion of the operating lever.

In a final variation, the operating lever includes a projecting portion, projecting from the handle. The outer portion of the flexible seal is attached to the handle adjacent to the operating lever, and the inner portion of the flexible seal is disposed about the projecting portion of the operating lever.

DETAILED DESCRIPTION OF THE INVENTION

1. Description of a Clip Applier

A clip applier for use in laparoscopic procedures in which insufflation is used and to which the gas seals according to the present invention may be applied will first be described referring to FIGS. 1A and 1B. This description is provided simply to illustrate the general type of two-component instrument to which the gas seals according to the invention can be applied. The gas seals according to the invention may be applied to any two-component instrument having a structure similar to that which will now be described.

Figure 1A:
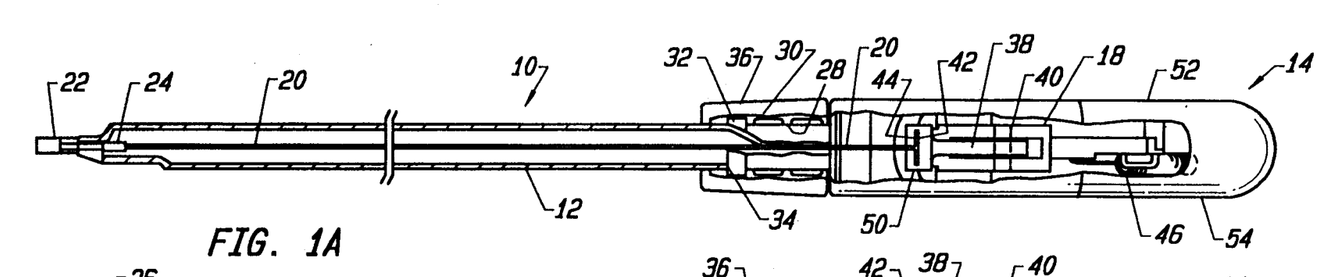
FIG. 1A is a horizontal cut-away view of a clip applier to which the gas-tight seals of the invention could be applied.
Figure 1B:
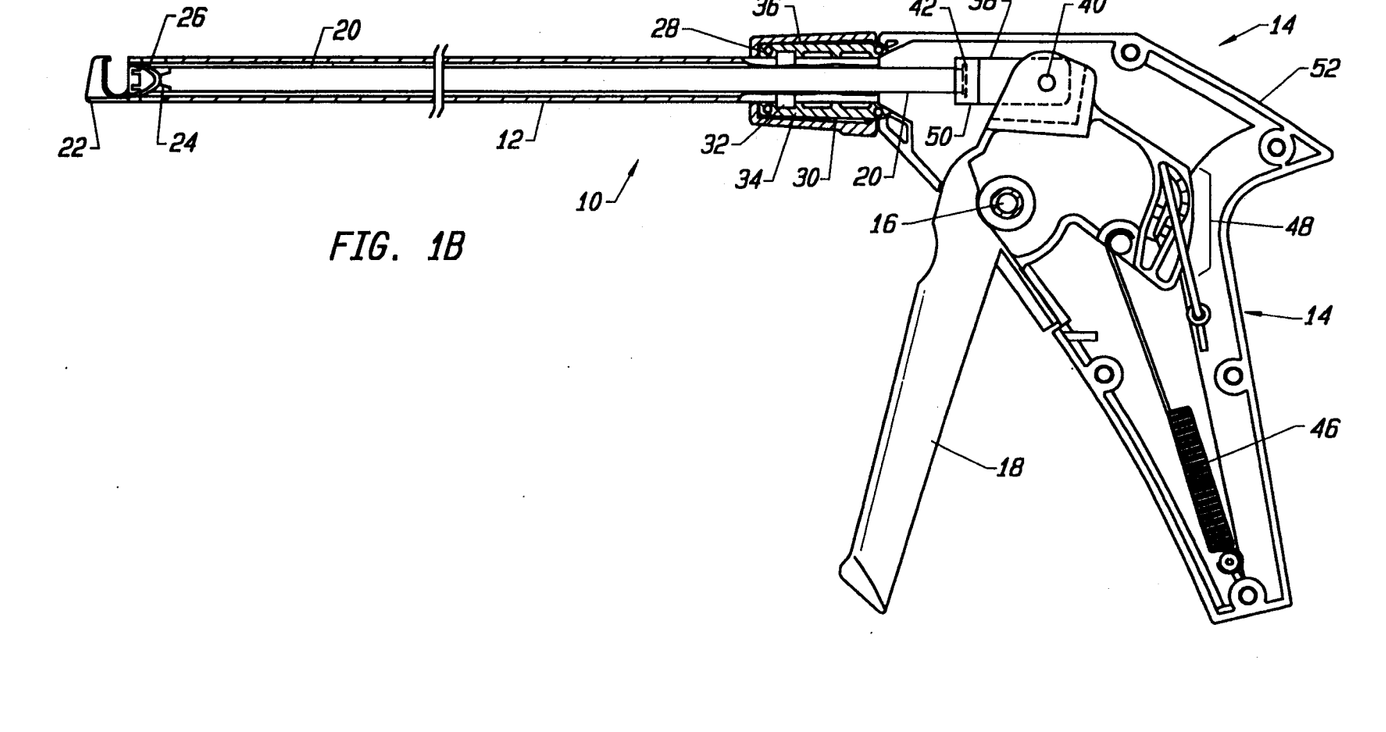
FIG. 1B is a vertical cross sectional view of the clip applier shown in FIG. 1A.

In FIGS. 1A and 1B, in the clip applier 10, the outer robe 12 is mounted in the handle 14. Mounted on a pivot 16 in the handle is the operating lever 18 to which is connected the operating rod 20.

At the distal end of the outer tube 12 is the anvil 22, which is the static part of the clip applier mechanism. At the distal end of the operating rod 20 is mounted the hammer 24, the moving part of the clip applier mechanism. A clip 26 is shown in position at the distal end of the outer tube 12. Drawing the operating lever towards the handle 14 slides the operating rod 20 distally inside the outer robe 12, which advances the hammer 24 and the clip 26 towards the anvil. In advancing towards the anvil, the clip rotates through 90 degrees, and then is flattened between the hammer and the anvil. The outer tube would normally include a magazine of several clips, and a mechanism for advancing the clips to the position shown, but these components have been omitted for simplicity.

So that the clip applier mechanism, or other mechanism, can be built into the outer tube 12, the outer tube is split longitudinally, and is made of two similar plastic moldings ultrasonically welded together.

The outer tube 12 is rotatably mounted in the bore 28 of the nose 30 of the handle 14. The flange 32 engages in an circumferential groove 34 in the bore 28 to locate the outer tube axially relative to the handle, and to allow the outer tube to rotate relative to the handle. The knob 36 is attached to the outer tube at a point distal of the nose 30 and extends proximally, surrounding the nose. The knob enables the clip applier mechanism to be rotated relative to the handle from a point near the handle. Alternatively, the outer tube 12 may be fixed in the handle.

The proximal end of the operating rod 20 is attached to the operating lever 18 by the rod driver 38, the proximal end of which is attached to the operating lever by the pivot 40. The distal end of the rod driver 38 is cylindrical, or has some other smooth, regular, and easy-to-seal surface, and will be called the piston 50. The proximal end of the operating rod carries a circular flange 42 which is trapped in the shouldered cylindrical aperture 44 formed in the piston. This arrangement allows the operating rod 20 to rotate, together with the outer tube, relative to the rod driver 38 when the knob 36 is rotated.

In the clip applier 10, the operating lever 18 is biassed into the position shown by the spring 46 placed between a point on the operating lever and a point on the handle. The ratchet mechanism 48 prevents the operating lever, once advanced towards the handle from the position shown, from returning to the position shown until it has been advanced all the way towards the handle, and a clip has been applied. This helps to prevent the mechanism jamming.

The handle is formed of two hollow plastic moldings 52 and 54, which are substantially mirror images of one another about the plane of FIG. 1B. The split handle arrangement enables most of the mechanism housed inside the handle 14 to be assembled in one of the moldings before the handle is completed by attaching the other molding to it, preferably by ultrasonic welding. Alternatively, the handle moldings can be attached together by a suitable adhesive.

The gas tight seals according to the invention are applied to the clip applier described in different ways: the rust through third embodiments provide direct sealing between the outer tube and the operating rod. These embodiments are preferred, since they do not require any of the handle to be gas tight. However, these embodiments are less practical when the operating rod has a complex shape, or comprises multiple elements, so that it is difficult to seal to.

The fourth through sixth embodiments provide a seal between the rod driver and the nose of the handle. Although these embodiments require that the nose of the handle be gas-tight, and, if the outer tube swivels relative to the handle, that a gas-tight swivel be provided between the outer tube and the nose of the handle, they are preferred when the operating rod is difficult to seal.

The seventh and eighth embodiments seal the aperture through which the operating lever projects from the handle. These embodiments require that all the handle be gas-tight, and, if the outer tube swivels relative to the handle, that a gas-tight swivel be provided between the outer tube and the nose of the handle. However, these embodiments are preferred when a difficult-to-seal operating rod prevents one of the first through third embodiments from being used, and when mechanism in the handle adjacent to the rod driver prevents the fourth through sixth embodiments from being used.

2. Gas-Tight Seals Between the Operating Rod and the Outer Tube (a) First Embodiment An instrument 100 incorporating a first embodiment of a gas-tight seal according to the invention is shown in FIGS. 2A through 2D. In this, the internal bellows seal 151 provides a seal between the outer tube 112 and the operating rod 120. The internal bellows seal 151 is made of a gas-tight, flexible material, such as silicone rubber, latex, or polyurethane. The internal bellows seal 151 is shaped such that its distal end 153 fits tightly over the proximal end of the outer tube 112, and its proximal end 155 fits tightly over the operating rod just proximal of the piston 150. In the example shown, the distal end 153 has a circular cross section and the proximal end 155 has a rectangular cross section. The proximal end and the distal end are attached to the operating rod and the outer tube, respectively, using a suitable adhesive to ensure a gas-tight seal.

The mid portion 157 of the internal bellows seal 151 tapers from the cross section of the proximal end 155 to the cross section of the distal end 153. The mid portion may also include accordion-like folds for greater flexibility.

Since the outer tube 112 and the operating rod 120 rotate together when the knob 136 is rotated, the internal bellows seal 151 does not have to accommodate any relative rotational motion between the operating rod and the outer tube.

The distal end 153 of the internal bellows seal fitting over the proximal end of the outer tube 112 increases the effective diameter of the proximal end of the outer tube slightly. Consequently, the handle moldings 152 and 154 have to be modified in the area indicated by the numeral 159 in Alternatively, the distal end 153 of the internal bellows seal 151 can be reduced so that it can be placed inside the proximal end of the outer tube 112, and pressed against the inner wall of the outer tube 112. This can be accomplished by compressing the wall of the seal between the outer diameter of a washer or grommet and the inner diameter of the proximal end of the outer tube, or by other suitable methods. This embodiment would also avoid the need to modify the outer diameter of the proximal end of the outer tube 112 as described above. This embodiment is preferred because it allows the internal bellows seal 151 to be attached to the outer tube 112 while preventing the bellows seal from interfering with the rotation of the outer tube in the handle.

Figure 2A:
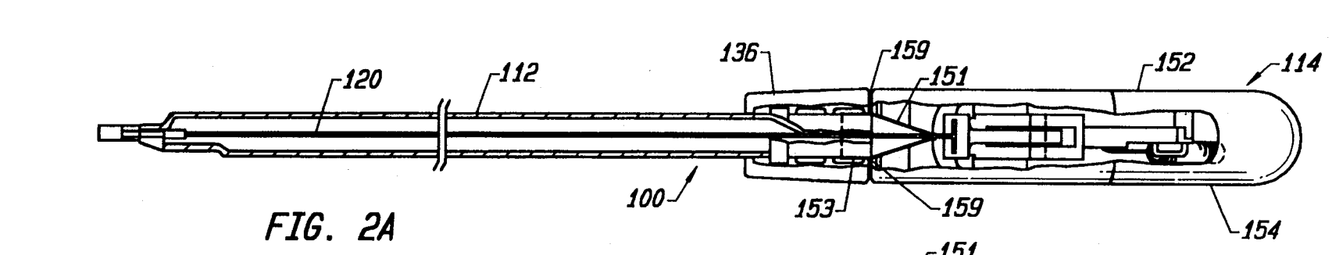
FIG. 2A is a horizontal cut-away view of a clip applier to which an internal bellows seal according to the first embodiment of a gas-tight seal according to the invention is applied.
Figures 2B, 2C, 2D:
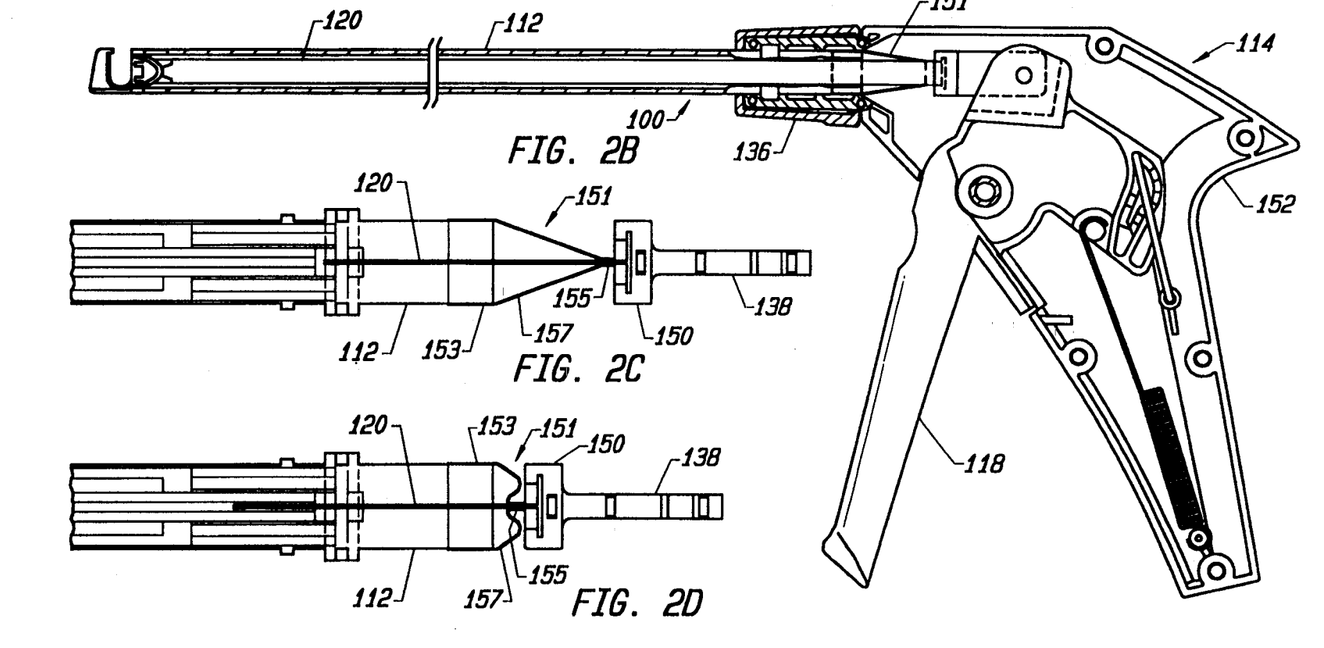
FIG. 2B is a vertical cross sectional view of the clip applier to which an internal bellows seal according to the first embodiment of a gas-tight seal according to the invention is applied.
FIG. 2C is a view of the proximal part of the outer tube, the operating rod, and the internal bellows seal according to the invention with the operating rod in its normal state.
FIG. 2D is a view of the proximal part of the outer tube, the operating rod, and the internal bellows seal according to the invention after the operating rod has been slid distally by operating the operating lever.

FIG. 2C shows the relative positions of the outer tube 112A, the operating rod 120, and the internal bellows seal 151 with the operating lever 118 in its normal position. The internal bellows seal 151 is shown in its distended state. FIG. 2D shows the relative positions of the outer tube, the operating rod, and the internal bellows seal after the operating lever has been moved towards the handle 114, which slides the operating rod 120 distally relative to the outer tube 112. The internal bellows seal 151 is shown in its compressed state.

With the arrangement shown, insufflation gas passes up the outer tube 112 as far as the internal bellows seal 151, but cannot escape. This is because the only potential escape route, i.e., between the operating rod 120 and the outer tube 112, has been made gas tight by the internal bellows seal 151. With the internal bellows seal 151, the outer tube/operating rod is made gas tight, which eliminates the need to provide any gas-tight sealing in the handle.

(b) Second Embodiment

Figures 3A, 3B, 3C, 3D, 3E:
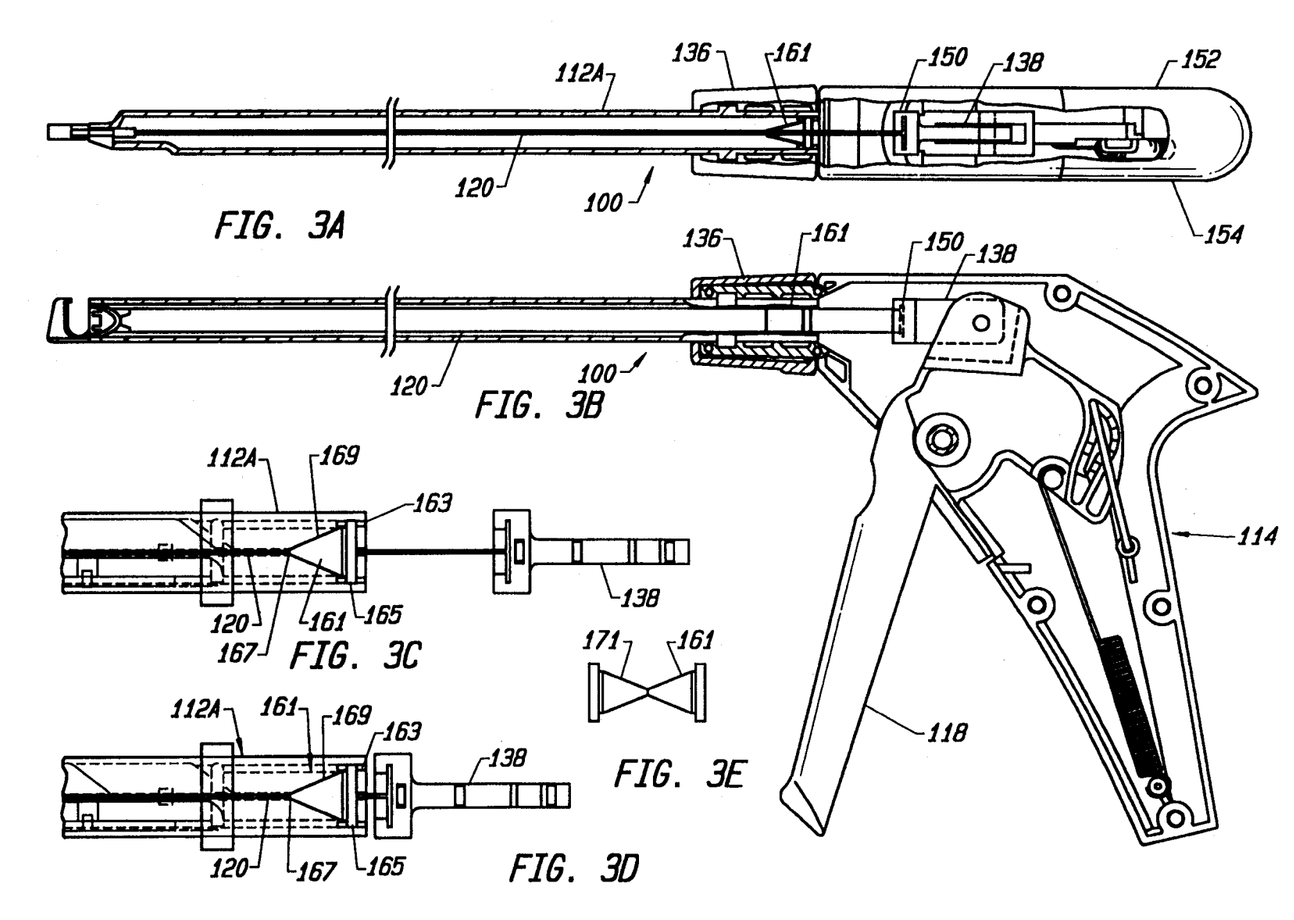
FIG. 3A is a horizontal cut-away view of a clip applier to which a duckbill seal according to the second embodiment of a gas-tight seal according to the invention is applied.
FIG. 3B is a vertical cross sectional view of the clip applier to which a duckbill seal according to the second embodiment of a gas-fight seal according to the invention is applied.
FIG. 3C is a view of the proximal part of the outer tube, the operating rod, and the duckbill seal according to the invention with the operating rod in its normal state.
FIG. 3D is a view of the proximal pan of the outer tube, the operating rod, and the duckbill seal according to the invention after the operating rod has been slid distally by operating the operating lever.
FIG. 3E shows an arrangement of a double duckbill seal.

An instrument 100A incorporating a second embodiment of a gas-tight sea/according to the invention is shown in FIGS. 3A through 3E. In this, the duckbill seal provides a seal between the bore of the outer tube 12A and the operating rod 120. The duckbill seal 161 is shown in FIG. 3C, and is made of a gas-tight, flexible material, such as silicone rubber, latex, or polyurethane. The duckbill seal 161 is shaped as shown such that its flanged portion 165 fits the seat 163 in the outer tube 112A, and its nose 167 is a sliding fit on the operating rod 120. A duckbill seal works best when the operating rod has a rectangular cross section as shown. The mid portion 169 of the duckbill seal 161 tapers from the ranged portion 165 to the nose 167.

The proximal end of the outer robe 112A is shaped to accommodate the duckbill seal 161, and to provide a seat 163 for the ranged portion 165 of the duckbill seal, as shown in detail in FIGS. 3C and 3D. The seat includes proximal and distal flanges to engage with the ranged portion 165 of the duckbill seal, so that the duckbill seal is positively located with respect to forces imposed upon it by the operating rod 120 sliding through it. The ranged portion 165 is attached to the seat 163 using a suitable adhesive.

The operating rod 120 slides through the nose 167 of the duckbill seal. The pressure of the insufflation gas against the outer surface of the nose of the duckbill seal presses the nose of the seal against the operating rod to provide a gas-tight seal. It is preferable to coat the inside surface of the duckbill seal with a silicone grease or oil to lubricate the seal so that the operating rod can slide freely through the seal.

Since the outer robe 112A and the operating rod 120 rotate together when the knob 136 is rotated, the duckbill seal 161 does not have to accommodate any relative rotational motion between the operating rod and the outer tube.

FIG. 3C shows the relative positions of the outer tube 112A, the operating rod 120, and the duckbill seal 161 with the operating lever 118 (FIG. 3B) in its normal position. FIG. 3D shows the relative positions of the outer tube, the operating rod, and the duckbill seal after the operating lever 118 been moved towards the handle 114, which slides the operating rod 120 distally relative to the outer tube 112A, and slides the operating rod 120 distally through the nose of the duckbill seal 161.

With the arrangement shown, insufflation gas passes up the outer tube 112A as far as the duckbill seal 161, but cannot escape. This is because the only potential escape route, i.e., between the operating rod 120 and the outer tube 112, has been made gas tight by the duckbill seal 161. The duckbill seal 161 makes the outer tube/operating rod unit gas-tight, and eliminates the need to seal the handle.

An additional degree of gas tightness can be provided by substituting two duckbill seals 161 and 171 for the single duckbill seal 161, as shown in FIG. 3E.

(c) Third Embodiment

An instrument 100B incorporating a third embodiment of a gas-fight seal according to the invention is shown in FIGS. 4A through 4D. The wiping seal 181 is attached to the bore of the proximal portion of the outer tube 112B, and includes plural flexible blades 199 that are transverse to the direction of motion of the operating rod and that contact opposite sides of the operating rod. The wiping seal thus provides a gas-tight seal between the operating rod 120 and the outer tube 112B.

Figure 4A:
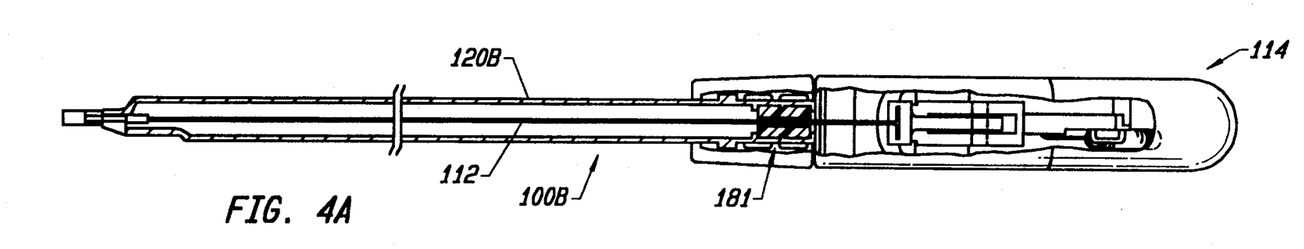
FIG. 4A is a horizontal cut-away view of a clip applier to which a wiping seal according to the third embodiment of a gas-tight seal according to the invention is applied.
Figures 4B, 4C, 4D:
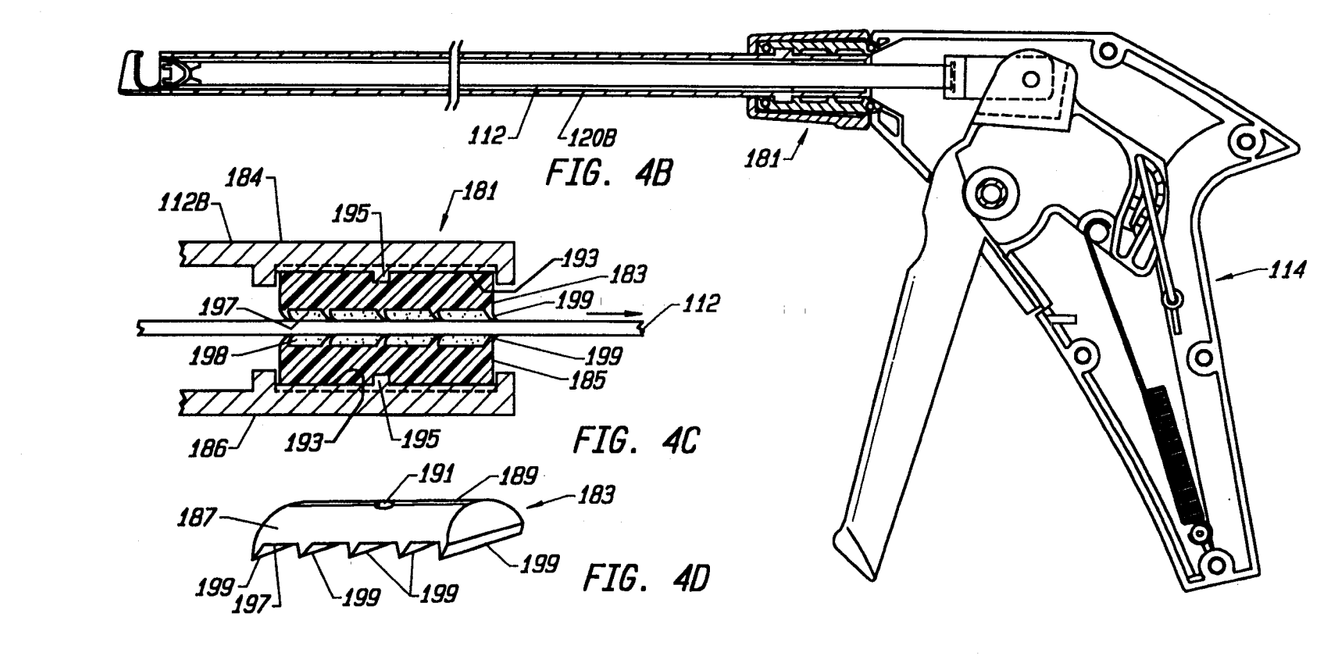
FIG. 4B is a vertical cross sectional view of the clip applier to which a wiping seal according to the third embodiment of a gas-tight seal according to the invention is applied.
FIG. 4C is a cross sectional view of the proximal pan of the outer tube, the operating rod, and the wiping seal according to the invention.
FIG. 4D is a perspective view of one of the wiping seal halves.

The wiping seal 181 is preferably split into two seal halves 183 and 185 located in opposite longitudinal halves of the outer tube 112B and disposed on opposite sides of the operating rod 120, as shown in FIG. 4C in which the proximal portion of the outer tube 112B is shown. Splitting the wiping seal facilitates molding and assembly.

Each outer tube molding 184 and 186 includes an internal semicylindrical region adjacent to its proximal end to accommodate one of the seal halves 183 and 185, respectively, as shown in FIG. 4C. A ridge 193 and a tab 195 is preferably included in the semi-cylindrical region of each outer tube molding to locate the seal halves 183 and 185 longitudinally and rotationally.

The seal half 183 is shown in detail in FIG. 4D. The seal half 183 is made of a soft, resilient material such as silicone rubber. It has the shape of a minor segment of a cylinder. Its curved outer surface 187 is shaped to fit in one half of the outer tube, and includes a groove 189 and a socket 191 that engage in the ridge 193 and the tab 195, respectively, in the semicylindrical portion of the outer tube molding 184.

The inner surface 197 of each seal half 183 and 185 carries a number of transverse blades 199, five in the preferred embodiment. The thickness of the seal halves and the length of the blades are such that the blades contact the operating rod, and there is a clearance between the inner surface 197 and the operating rod.

The curved outer surface 187 of each seal half is coated with silicone grease before the seal half is inserted into its respective outer tube molding. The silicone grease provides a gas-tight seal between the seal half and the outer tube. Alternatively, the seal half can be attached to the outer tube molding with a suitable adhesive. The space between the blades 199 is fried with silicone grease 198 to provide lubrication, and to perfect the gas tightness of the seal between the seal halves and the operating rod, and between the two seal halves.

The multiple blades 199, and the wiping action between the blades and the operating rod 120, retain the silicone grease within the wiping seal, and provide a seal that remains gas-tight over many operating cycles, if required.

With the arrangement shown, insufflation gas passes up the outer tube 112B as far as the wiping seal 181, but cannot escape. This is because the only potential escape mutes, i.e., between the operating rod 120 and wiping seal 181, and between the wiping seal and the outer tube 112B, have been made gas tight. The wiping seal 181 makes the outer tube/operating rod unit gas-fight, and eliminates the need to seal any part of the handle 114.

3. Gas-tight Seals Between the Rod Driver and the Handle (a) Fourth Embodiment

Figure 5A:
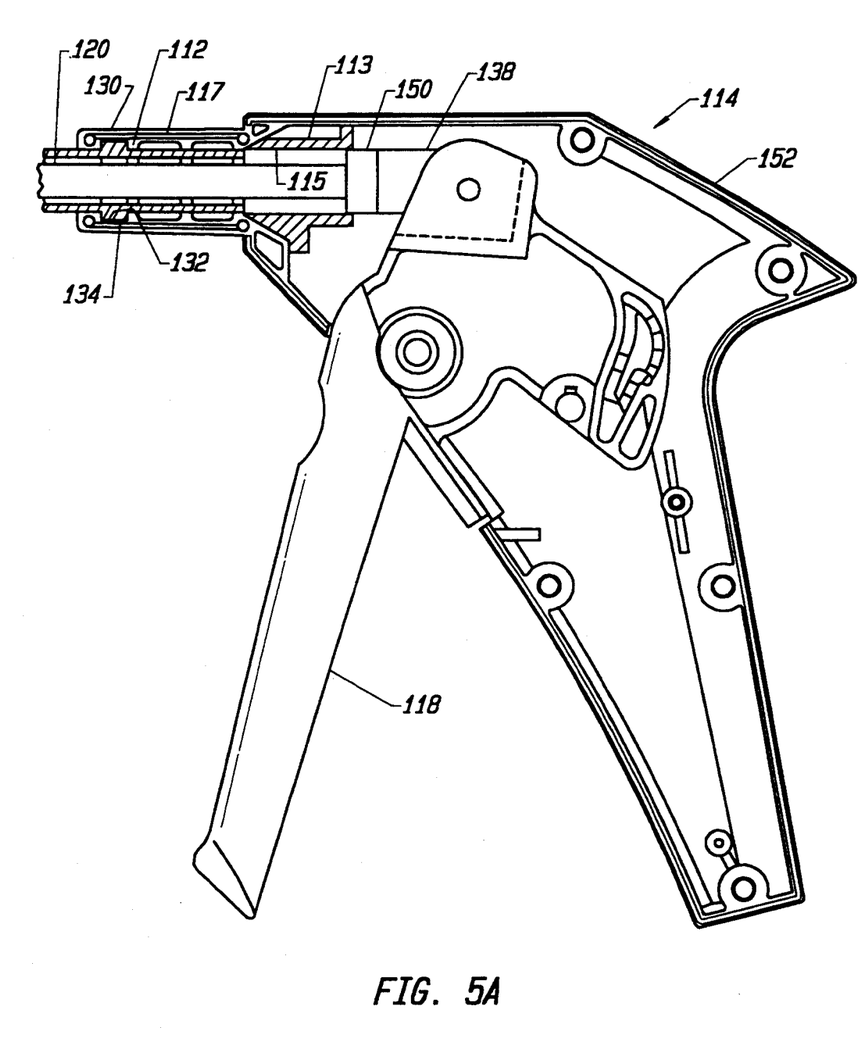
FIG. 5A is a vertical cross sectional view of a clip applier to which a piston seal according to the fourth embodiment of a gas-fight seal according to the invention is applied. The operating lever is in its normal position.
Figure 5B:
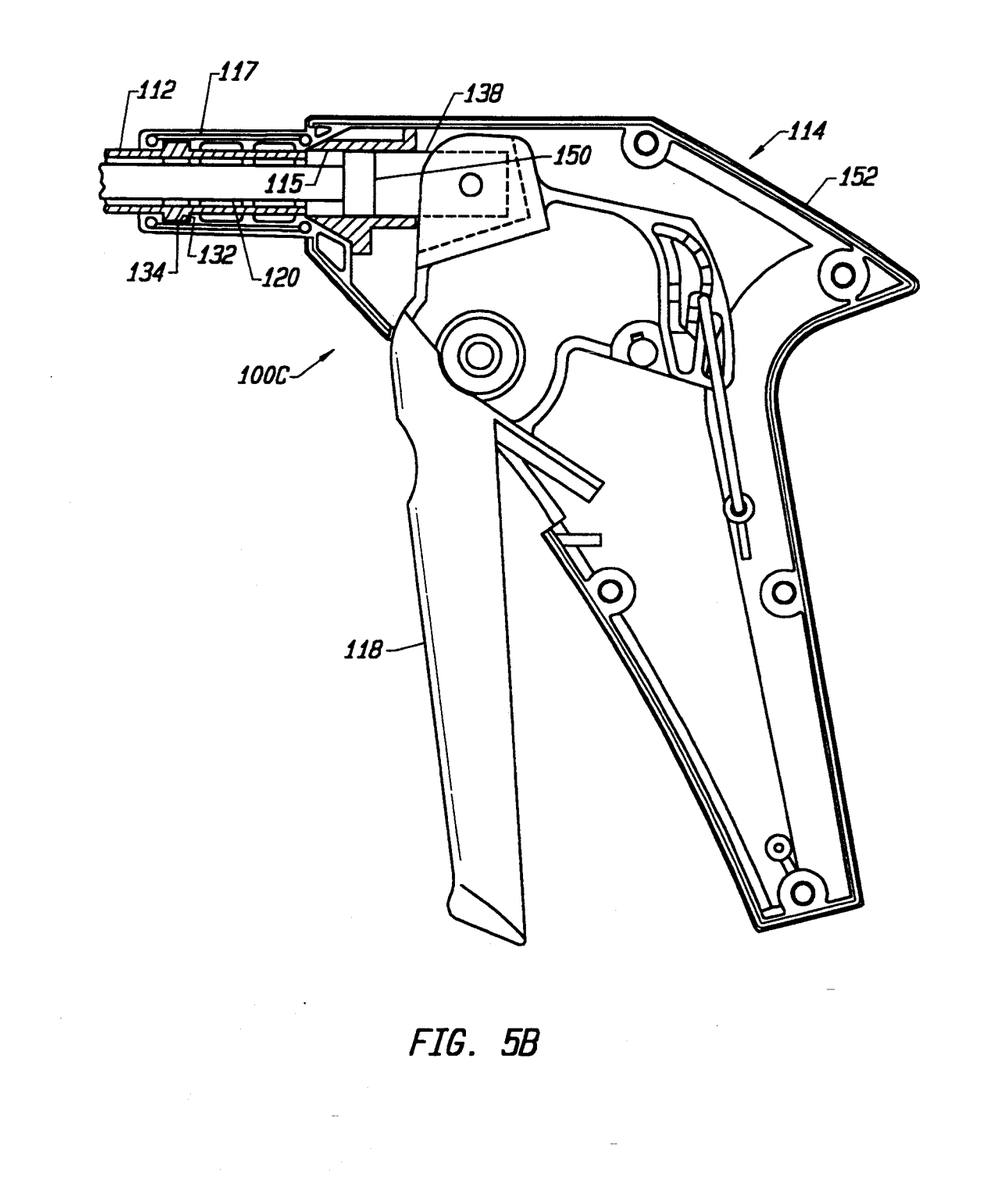
FIG. 5B is a vertical cross sectional view of a clip applier to which a piston seal according to the fourth embodiment of a gas-tight seal according to the invention is applied. The operating lever is shown in its operated position, closer to the handle than in FIG. 5A.

In the instrument 100C incorporating a fourth embodiment of a gas-tight seal according to the invention shown in FIGS. 5A and 5B, a piston seal is located in the handle 114.. A block 113, which is preferably a plastic molding, having a cylindrical bore 115 is installed in the handle in the position shown. The block is made of ABS, or some other suitable plastic. The bore 115 is threaded or corrugated to help the bore retain grease.

The block 113 is installed in the handle 114 such that a gas-fight seal is formed between the handle and the block. This can be achieved by cementing the block in place using a suitable adhesive. Preferably, however, the outer surface of the block is coated with silicone grease, and the block is put in place inside the handle. The block is held in position by engaging locating ears molded in the block with the handle, and the silicone grease forms the gas-tight seal between the block and the handle. Alternatively, the handle moldings (handle molding 152 is shown) can be modified such that, when the handle moldings are assembled to form the handle, a gas-tight structure with a cylindrical bore similar to the bore 115 is formed.

The bore 115 of the block 113 is sized such that the cylindrical distal portion of the rod driver 138, which will be called the piston 150, is a sliding fit inside the bore. Before the piston is inserted into the bore, the bore is coated with a suitable silicone grease to lubricate the piston seal.

The silicone grease can be anything from a viscous stop-cock grease to a lubricant grease. The type of grease used, and the clearance between the bore 115 and the piston 150 can be chosen according to the desired "feel" of the instrument, i.e., the force required to operate the operating lever, and whether or not the operating lever stays in position when the force is removed.

Because the gas-tight seal is located in the handle 114, the nose 130 of the handle, and the junction between the outer robe 112 and the handle 114, must also be made gas-tight. The nose 130 is made gas-tight by including the energy director 117 in one of the handle moldings (the energy director 117 in the handle molding 152 is shown). The energy director 117, which is well known in the ultrasonic welding art, aids the ultrasonic welding process by which the two handle moldings are joined together, ensuring that the weld extends uniformly along the whole of the periphery of the nose without any voids.

The junction between the outer robe 112 and the handle 114 is made gas-fight by applying a suitable silicone grease to the circumferential groove 134 in the nose 130 of the handle before the flange 132 is inserted into the groove. Alternatively, or additionally, an 0-ting seal (not shown) can be included between the flange 132 and the circumferential groove 134 in the nose 130.

With the arrangement shown, insufflation gas passes up the outer tube 112 into the nose 130, and the block 113, but cannot escape. This is because all the potential escape routes, i.e., the junction of the handle moldings 152 and 154 in the nose 130, the junction between the nose 130 and the block 113, the junction between the block and the piston 150, and the junction between the nose 130 and the outer tube 112, have been made gas tight.

(b) Fifth Embodiment

Figure 6:
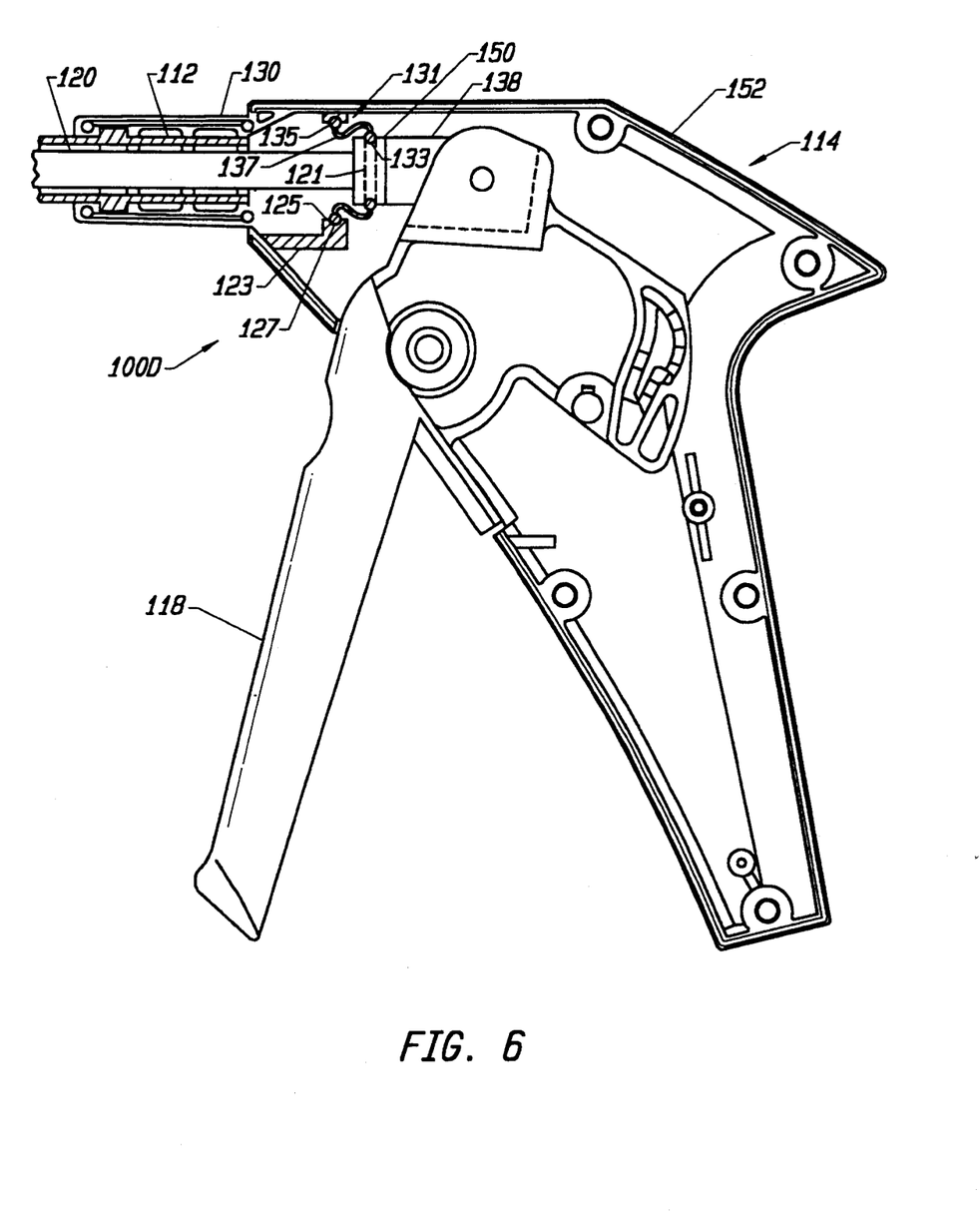
FIG. 6 is a vertical cross sectional view of a clip applier to which a diaphragm seal according to the fifth embodiment of a gas-tight seal according to the invention is applied.

An instrument 100D incorporating a fifth embodiment of a gas-tight seal according to the invention is shown in FIG. 6. In FIG. 6, a circumferential groove 121 is formed in the cylindrical surface of the piston 150. An insert 123 is fitted into the handle moldings (the handle molding 152 is shown) and forms a gas-tight seal with them. The insert 123 has a substantially circular bore 125, which is preferably substantially concentric with the piston 150. The circumferential groove 127 is formed in the wall of the bore 125. The circumferential groove 127 is positioned along the axis defined by the operating rod 120 such that it is about half way along the travel of the circumferential groove 121 when the operating lever 118 is operated. It maybe necessary to modify the handle moldings to accommodate the insert.

The diaphragm seal 131 engages in the circumferential groove 121 in the piston 150, and in the circumferential groove 127 in the insert 123, and forms a gas-tight seal between them. The diaphragm seal 131 is made of silicone rubber, latex, polyurethane, or some other suitable flexible material. The diaphragm seal 131 is molded with a thickened inner periphery 133 that snaps into the circumferential groove 121.

The outer periphery of the diaphragm seal is attached to the annulus 135. The annulus 135 is made of metal or stiff plastic, and engages with the circumferential groove 127. The annulus 135 can be molded in with the diaphragm seal 131, or the diaphragm seal 131 can be bonded to the annulus 135 using a suitable adhesive. The diaphragm seal may be molded in polyurethane, in which case, it may be molded with a thickened outer periphery, and the separate annulus can be dispensed with. The thickened outer periphery of a polyurethane molding is sufficiently stiff to stay engaged with the circumferential groove 127 when the piston 150 is moved axially.

The mid portion 137 of the diaphragm seal 131 is sufficiently flexible to accommodate the axial movement of the piston 150. To this end, the mid portion 137 of the diaphragm seal 131 may be folded similarly to the mid portion 147 of the seal 1.41 shown in FIG. 7.

Alternatively, and preferably, the insert 123 may be dispensed with and the handle moldings modified so that they each include one half of a circumferential groove similar in configuration and location to the circumferential groove 127. The circumferential groove would accommodate a diaphragm seal similar to the diaphragm seal 131.

In the embodiments shown in FIG. 6, the nose 130 and the junction between the nose 130 and the outer tube 112 are made gas-tight, as already described.

With the arrangement shown, insufflation gas passes up the outer tube 112, into the nose 130, as far as the diaphragm seal 131, but cannot escape. This is because all the potential escape routes, i.e., the junction of the handle moldings 152 and 154 in the nose 130, the junction between the nose 130 and the insert 123, the junction between the insert and the diaphragm seal 131, the junction between the diaphragm seal and the piston 150, and the junction between the nose 130 and the outer tube 112, have been made gas tight.

(c) Sixth Embodiment

Figure 7:
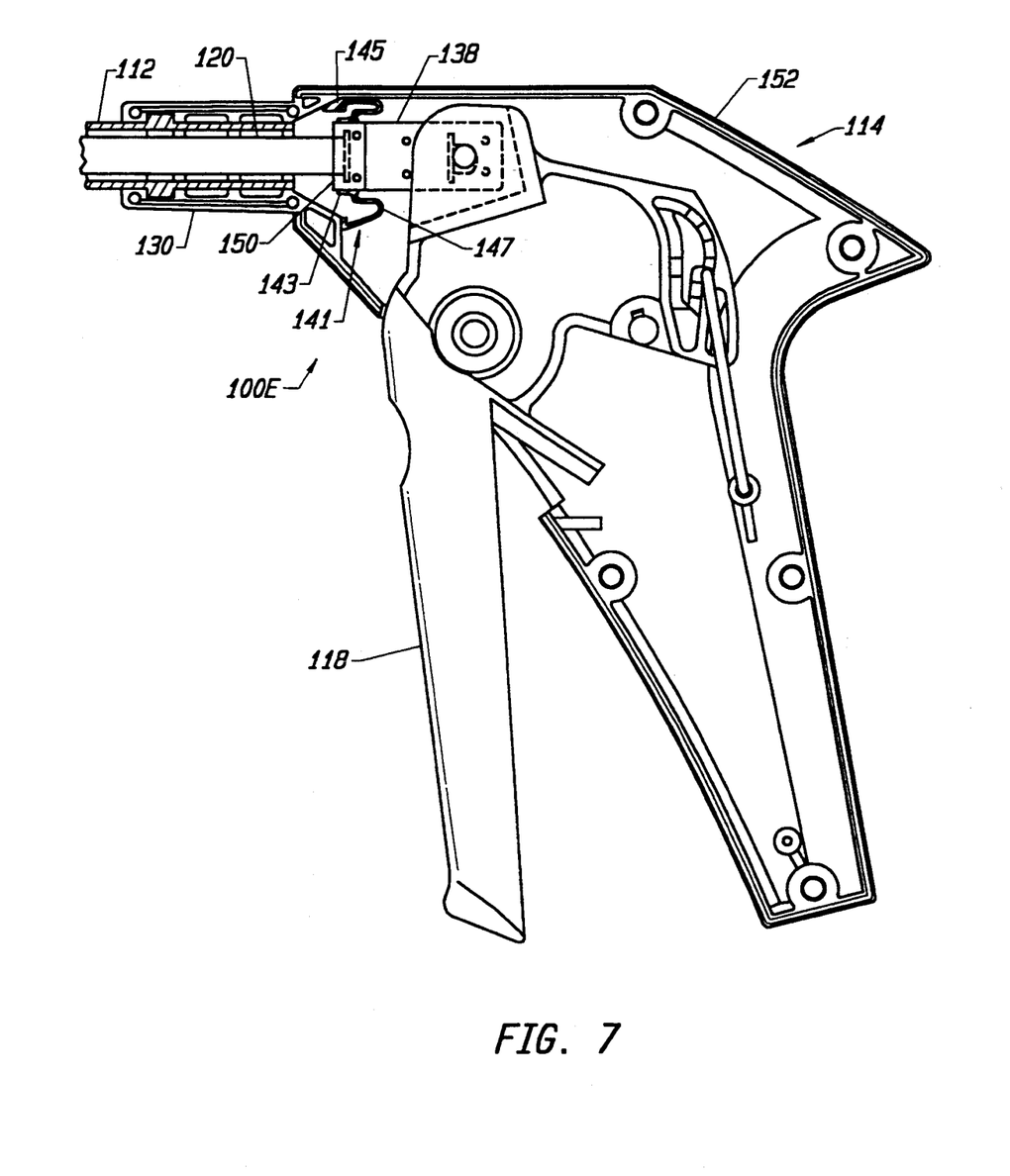
FIG. 7 is a vertical cross sectional view of a clip applier to which a seal according to the sixth embodiment of a gas-tight seal according to the invention is applied.

An instrument 100E incorporating a sixth embodiment of a gas-tight seal according to the invention is shown in FIG. 7. The sixth embodiment is similar to the fifth embodiment, but it is simpler to implement because no insert is required, and there is no need to modify the rod driver molding or the handle moldings. Insufflation gas is prevented from escaping by the seal 141 which provides a seal between the handle 114 and the piston 150 on the rod driver 138. The seal 141 is preferably made of an elastomeric material, such as latex, silicone rubber, polyurethane, or PTFE.

The seal 141 is molded with the collar 143 at its inner periphery into which the piston 150 fits tightly, thereby forming a gas-tight seal. The collar 143 may be affixed to the piston using a suitable adhesive.

The outer periphery of the seal 141 is attached to the annulus 145. The annulus 145 is made of metal or stiff plastic, and is shaped to fit closely to the contours of the inside of the handle molding as shown. The annulus 145 can be molded in with the seal 141, or the seal 141 can be bonded to the annulus 145 using a suitable adhesive. The annulus 145 is then attached to the inside of the handle moldings (the handle molding 152 is shown)

using a suitable adhesive to form a gas-tight seal with the handle moldings.

The mid portion 147 of the seal 141 is folded as shown to allow the seal to flex easily to accommodate the axial movement of the rod driver 138 as the operating lever 118 is operated.

The nose 130 and the junction between the nose 130 and the outer robe 112 are made gas-fight, as already described.

With the arrangement shown, insufflation gas passes up the outer robe 112, into the nose 130, as far as the seal 141, but cannot escape. This is because all the potential escape routes, i.e., the junction of the handle moldings 152 and 154 in the nose 130, the junction between the handle 114 and the outer periphery of the seal 141, the junction between the collar 143 and the piston 150, and the junction between the nose 130 and the outer tube 112, have been made gas tight.

Figure 8:
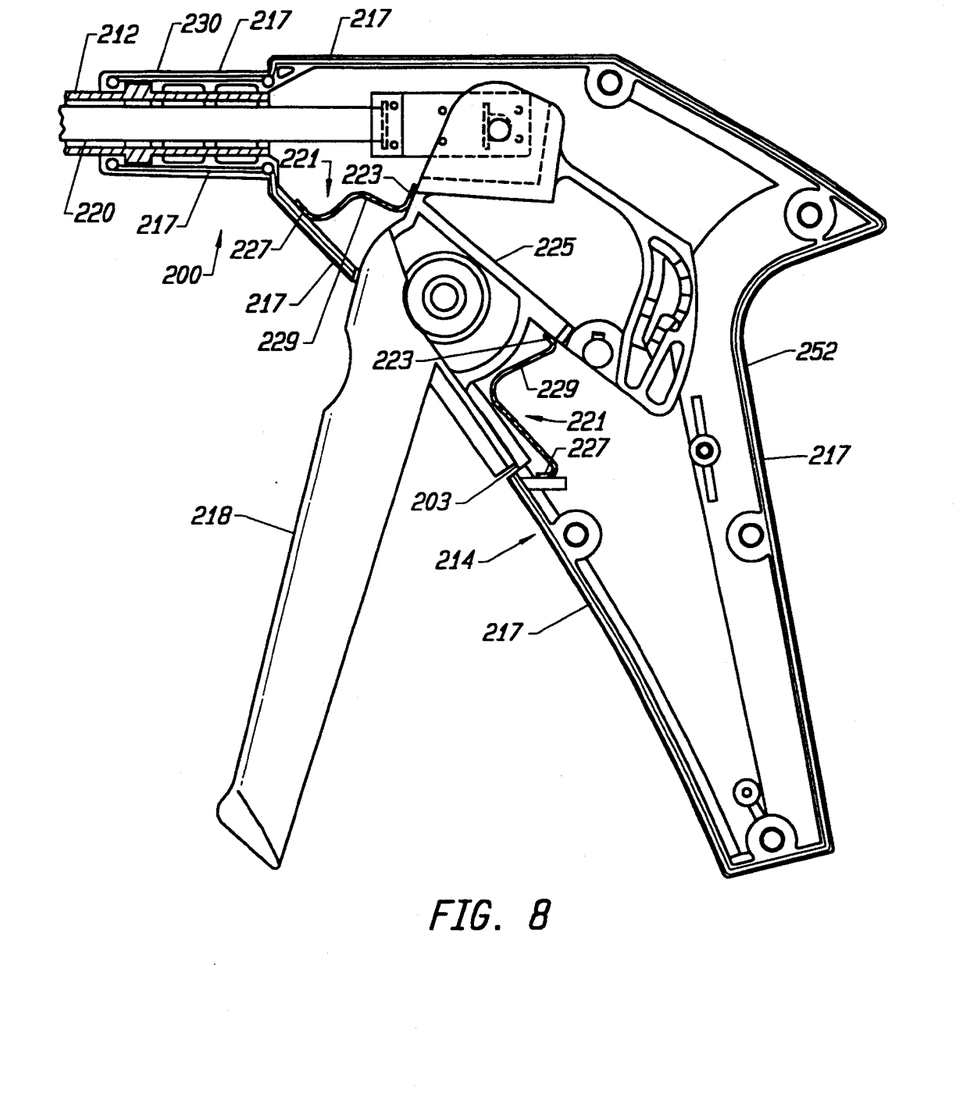
FIG. 8 is a vertical cross sectional view of a clip applier to which an aperture seal according to the seventh embodiment of a gas-tight seal according to the invention is applied.

4. Gas-Tight Seals Between the Handle and the Operating Lever (a) Seventh Embodiment An instrument 200 incorporating a seventh embodiment of a gas-tight seal according to the invention is shown in FIG. 8. In this, the handle moldings are attached to one another to form a gas-tight seal. To achieve this, the energy director 217 is included along the entire periphery of one of the handle moldings (the handle molding 252 is shown). The energy director 217 aids the ultrasonic welding process by which the two handle moldings are joined together, ensuring that the weld extends uniformly along the whole of the periphery of the handle moldings without any voids.

The aperture 203, through which the operating lever 218 projects from the handle 214, is not sealed by welding the handle moldings together. In this embodiment, insufflation gas is prevented from escaping through the aperture 203 by the aperture seal 221, which forms a seal between the operating lever 218 and the handle 214. The aperture seal 221 is preferably made of an elastomeric material, such a latex, silicone rubber, polyurethane, or PTFE.

The aperture seal 221 is molded with the collar 223 at its inner periphery, into which the operating lever 218 fits tightly as shown, thereby forming a gas-tight seal. The collar 223 is affixed to the operating lever using a suitable adhesive. Also, it is preferable to modify the operating lever molding to add the rib 225 to make the operating lever a simpler shape to seal to. This simplifies the shape of the collar 223, and improves the effectiveness of the gas-tight seal between the collar 223 and the operating lever 218.

The outer periphery of the aperture seal 221 is attached to the annulus 227. The annulus 227 is made of metal or stiff plastic, and is shaped to fit closely to the contours of the inside of the handle molding as shown. The annulus 227 can be molded in with the seal 221, or the seal 221 can be bonded to the annulus 227 using a suitable adhesive. The annulus 227 is then attached to the inside of the handle moldings (the handle molding 252 is shown) using a suitable adhesive to form a gastight seal with the handle 214.

The mid portion 229 of the seal 221 is folded as shown to allow the seal to flex easily to accommodate the movement of the operating lever 218 as the operating lever is operated.

With the arrangement shown, insufflation gas passes up the outer tube 212, into the nose 230, and the handle 214, but cannot escape. This is because all the potential escape routes, i.e., the junction of the handle moldings 252 and 254, the junction between the handle 214 and the aperture seal 221, the junction between the aperture seal 221 and the operating lever 218, and the junction between the nose 230 and the outer tube 212, have been made gas tight.

(b) Eighth Embodiment

Figures 9A, 9B:
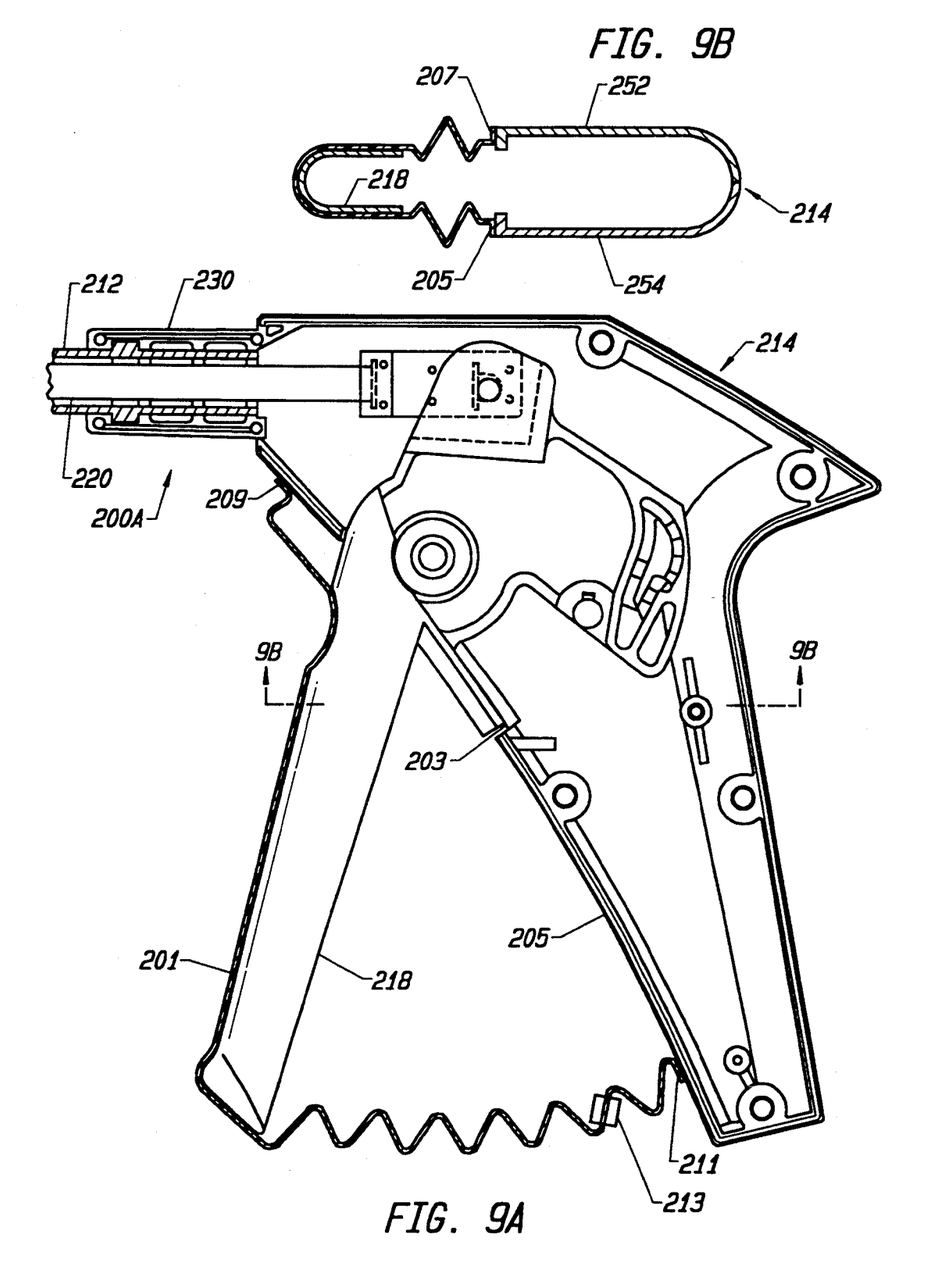
FIG. 9A is a vertical cross sectional view of a clip applier to which an external bellows seal according to the eighth embodiment of a gas-tight seal according to the invention is applied.
FIG. 9B is a transverse cross sectional view, on the line shown in FIG. 9A, of a clip applier to which a piston seal according to the eighth embodiment of a gas-tight seal according to the invention is applied.

An instrument 200A incorporating an eighth embodiment of a gas-tight seal according to the invention is shown in FIGS. 9A and 9B. In this embodiment, the handle moldings are attached to one another to form a gas-tight seal, as described above. Also, as stated above, the aperture 203, through which the operating lever 218 projects from the handle 214, is not sealed by welding the handle moldings together. In this embodiment, the aperture 203 and the operating lever 218 are enclosed by the external bellows seal 201. The external bellows seal 201 is preferably made of silicone rubber, but may be made of any other flexible plastic. A small external bellows seal enclosing the aperture 203 and only a pan of the operating lever 218 could be used. However, the larger external bellows seal 201 shown, which encloses all of the operating lever and extends beyond the aperture 203 is preferred because it is simpler to attach to the handle, and eliminates a junction between the external bellows seal and the operating lever. Alternatively, the external bellows seal can envelop all of the handle 214. The external bellows seal preferably includes the accordion folds shown.

The external bellows seal 201 is attached to the handle 214 on either side of the operating lever 218, along the lines indicated by the numerals 205 and 207 in FIG. 9B. The external bellows seal is also attached to the handle 214 above and below the operating lever along lines indicated by the numerals 209 and 211. The external bellows seal 201 is preferably attached to the handle by a suitable adhesive.

The external bellows seal 201 tends to act as a pump, pumping insufflation gas down the outer tube into the body cavity in which the . Instrument is used when the operating lever 218 is moved towards the handle 214, and drawing insufflation gas and/or other fluids up the outer tube from the body cavity when the operating lever is released. To prevent this, the external bellows seal 201 is fitted with the pressure regulator 213, which is connected to the supply of gas (not shown) insufflating the body cavity in which the instrument is being used. The valve 213 keeps the pressure inside the handle 214 substantially equal to the pressure inside the body cavity, releasing insufflation gas into the atmosphere when the operating lever is moved towards the handle, and re-filling the handle with insufflation gas drawn from the insufflation gas supply when the operating lever is released.

With the arrangement shown, insufflation gas passes up the outer tube 212, into the nose 230, the handle 214, and the external bellows seal 201, but cannot escape. This is because all the potential escape routes, i.e., the junction of the handle moldings 252 and 254, the junction between the handle 214 and the external bellows seal 201, .and the junction between the nose 230 and the outer tube 212, have been made gas tight.

Although the foregoing invention has been described in detail for purposes of clarity of understanding, it will be obvious that certain modifications may be practiced within the scope of the appended claims.

We claim:

1. An instrument for use in laparoscopic procedures in a body cavity insufflated with a gas, the instrument comprising:
   a static portion including:
   a handle, and
   an elongate outer tube having a bore, a proximal portion attached to the handle, and a distal portion adapted for inserting into the body cavity;
   a moving portion including:
   an operating lever pivotally mounted in the handle, and
   an elongate operating rod mounted in the bore of the elongate outer tube, and axially slidable relative thereto in response to the operating lever; and
   a flexible sealing means for preventing the gas from escaping from the body cavity via the static portion, the flexible sealing means including:
   an outer portion fixedly attached to at least one of the handle and the elongate outer tube of the static portion,
   an inner portion disposed about part of at least one of the operating lever and elongate operating rod of the moving portion, the inner portion being movable relative to the outer portion, and
   a flexible mid portion interconnecting the outer portion and the inner portion, the flexible mid portion permitting the inner portion to move relative to the outer portion.

2. The instrument of claim 1, wherein:
   the flexible sealing means extends into the handle from the proximal portion of the outer tube,
   the outer portion of the flexible sealing means is attached concentrically to the proximal portion of the outer tube, and
   the inner portion of the flexible sealing means is disposed about the operating rod.

3. The instrument of claim 2, additionally comprising:
   a first adhesive means for attaching the outer portion of the flexible sealing means to the proximal portion of the outer tube, and
   a second adhesive means for attaching the inner portion of the flexible sealing means to the operating rod.

4. The instrument of claim 2, wherein:
   the outer tube includes a proximal end, and
   the outer tube has a reduced diameter adjacent to the proximal end to accommodate the outer portion of the flexible sealing means.

5. The instrument of claim 2, wherein the mid portion of the flexible sealing means is accordion folded.

6. The instrument of claim 1, wherein:
   the flexible sealing means comprises a duckbill seal accommodated in the bore of the proximal portion of the outer tube, the duckbill seal having a ranged portion and a nose,
   the ranged portion of the duckbill seal is attached to the bore of the proximal portion of the outer tube, and
   the nose portion of the duckbill seal is disposed about the operating rod, the operating rod sliding within the nose portion.

7. The instrument of claim 6, wherein:
   the duckbill seal is a first duckbill seal having a first nose, and
   the flexible sealing means additionally comprises a second duckbill seal disposed within the outer tube, the second duckbill seal having a second nose facing the first nose.

8. The instrument of claim 6, wherein the bore of the proximal portion of the outer tube includes a seat adapted for accommodating the ranged portion of the duckbill seal.

9. The instrument of claim 1, wherein:
   the operating lever includes a piston coupled to the operating rod, and
   the inner portion of the flexible sealing means is disposed about the piston.

10. The instrument of claim 9, wherein:
    the handle includes an inner surface adjacent to the piston,
    the outer portion of the flexible sealing means includes an annulus shaped to be attached to the inner surface of the handle adjacent to the piston, and
    the instrument additionally comprises an adhesive means for attaching the annulus to the inner surface of the handle adjacent to the piston.

11. The instrument of claim 9, wherein:
    the static portion additionally comprises an insert sealed within the handle, the insert having a bore disposed about the piston, the bore having an internal circumferential groove,
    the outer portion of the flexible sealing means includes an annulus, and
    the annulus engages in the internal circumferential groove.

12. The instrument of claim 11, wherein the annulus is made of a stiff material selected from a group including plastic and metal.

13. The instrument of claim 9, wherein:
    the handle includes a handle molding, the handle molding including an internal circumferential groove disposed substantially about the piston,
    the outer portion of the flexible sealing means includes an annulus, and
    the annulus engages in the internal circumferential groove.

14. The instrument of claim 13, wherein the annulus is made of a stiff material selected from a group including plastic and metal.

15. The instrument of claim 9, wherein the mid portion of the flexible sealing means is folded.

16. The instrument of claim 9, wherein:
    the piston includes an external circumferential groove, and
    the inner portion of the flexible sealing means is adapted to fit in the external circumferential groove in the piston.

17. The instrument of claim 16, wherein:
    the handle includes an inner surface adjacent to the piston,
    the outer portion of the flexible sealing means includes an annulus shaped to be attached to the inner surface of the handle adjacent to the piston, and
    the instrument additionally comprises an adhesive means for attaching the annulus to the inner surface of the handle adjacent to the piston.

18. The instrument of claim 16, wherein:
    the static portion additionally comprises an insert sealed within the handle, the insert having a bore disposed substantially about the piston, the bore having an internal circumferential groove, the outer portion of the flexible sealing means includes an annulus, and the annulus engages in the internal circumferential groove.

19. The instrument of claim 18, wherein the annulus is made of a stiff material selected from a group including plastic and metal.

20. The instrument of claim 16, wherein:

the handle includes a handle molding, the handle molding including an internal circumferential groove disposed substantially about the piston, the outer portion of the flexible sealing means includes an annulus, and the annulus engages in the internal circumferential groove.

21. The instrument of claim 20, wherein the annulus is made of a stiff material selected from a group including plastic and metal.

22. The instrument of claim 16, wherein the mid portion of the flexible sealing means is folded.

23. The instrument of claim 9, wherein the inner portion of the flexible sealing means includes a collar adapted to accommodate the piston.

24. The instrument of claim 23, additionally comprising an adhesive means for attaching the collar to the piston.

25. The instrument of claim 1, wherein:

the operating lever includes an internal portion housed within the handle, the outer portion of the flexible sealing means is attached within the handle adjacent to the operating lever, and the inner portion of the flexible sealing means is disposed about the internal portion of the operating lever.

26. The instrument of claim 25, wherein:

the handle includes an inner surface adjacent to the operating lever, and the instrument additionally comprises an adhesive means for attaching the outer portion of the flexible sealing means to the inner surface of the handle adjacent to the operating lever.

27. The instrument of claim 26, wherein the outer portion of the flexible sealing means includes an annulus shaped to be attached to the inner surface of the handle adjacent to the operating lever.

28. The instrument of claim 27, wherein the annulus is made of a stiff material selected from a group including plastic and metal.

29. The instrument of claim 25, wherein:

the inner portion of the operating lever includes a rib shaped to seal with the inner portion of the flexible sealing means, the inner portion of the flexible sealing means includes a collar, and the instrument additionally comprises an adhesive means for attaching the collar to the rib.

30. The instrument of claim 1, wherein:

the operating lever includes a projecting portion projecting from the handle, the outer portion of the flexible sealing means is attached to the handle adjacent to the operating lever, and the inner portion of the flexible sealing means is disposed about the projecting portion of the operating lever.

31. The instrument of claim 30, wherein the mid portion of the flexible sealing means is folded.

32. The instrument of claim 30, wherein the flexible sealing means includes a valve means for preventing a reduction of gas pressure in the handle when the operating lever is released.

33. The instrument of claim 32, wherein the valve means is additionally for preventing an increase in gas pressure in the handle when the operating lever is operated.

34. The instrument of claim 1, wherein:

the flexible sealing means comprises a wiping seal disposed in the bore of the proximal portion of the elongate outer tube, the wiping seal having a curved outer portion and a ribbed inner portion, the curved outer portion of the wiping seal is attached to the bore of the proximal portion of the elongate outer tube, and the ribbed inner portion is disposed about the operating rod, the operating rod sliding within the ribbed inner portion.

35. The instrument of claim 34, wherein the wiping seal comprises a pair of half seals disposed within the bore of the proximal portion of the outer tube on opposite sides of the operating rod.

36. The instrument of claim 34, wherein the ribbed inner portion includes:

a substantially flat surface substantially parallel to the operating rod, and plural flexible ribs projecting from the flat surface and contacting the operating rod.

37. The instrument of claim 36, wherein the ribbed inner portion additionally includes silicone grease disposed between the plural flexible ribs.

38. The instrument of claim 34, wherein the bore of the proximal portion of the outer tube and the curved outer portion of the wiping seal include mating portions to locate the wiping seal longitudinally and rotationally.

* * * * *